(12) United States Patent
Johnson

(10) Patent No.: US 8,011,634 B1
(45) Date of Patent: Sep. 6, 2011

(54) OXYGEN TANK ACCESSORY APPARATUS

(76) Inventor: Dale A. Johnson, Twin Lake, MI (US)

( * ) Notice: Subject to any disclaimer, the term of this patent is extended or adjusted under 35 U.S.C. 154(b) by 253 days.

(21) Appl. No.: 12/543,729

(22) Filed: Aug. 19, 2009

(51) Int. Cl.
*A47F 5/00* (2006.01)

(52) U.S. Cl. ............... 248/309.1; 248/313; 224/434

(58) Field of Classification Search ......... 248/309.1, 248/682, 687, 689, 302, 313, 316.1, 316.5, 248/229.1, 229.23, 230.4, 231.61; 211/89.01, 211/120, 124; 220/491, 485; 224/434
See application file for complete search history.

(56) References Cited

U.S. PATENT DOCUMENTS

| | | | | |
|---|---|---|---|---|
| 2,331,211 A * | 10/1943 | Lyman | ............ | 224/448 |
| 2,554,865 A * | 5/1951 | Lydick | ............ | 224/434 |
| 3,513,970 A * | 5/1970 | Eckholm, Jr. | ............ | 206/150 |
| 3,603,550 A * | 9/1971 | Byrd | ............ | 248/313 |
| 3,780,972 A * | 12/1973 | Brodersen | ............ | 248/313 |
| 3,823,907 A * | 7/1974 | Ziaylek, Jr. | ............ | 248/313 |
| 3,970,344 A * | 7/1976 | Baumann | ............ | 297/188.02 |
| 4,586,687 A * | 5/1986 | Ziaylek, Jr. | ............ | 248/313 |
| D305,629 S | 1/1990 | Wood | | |
| 5,288,001 A | 2/1994 | Locarno | | |
| 6,220,557 B1 * | 4/2001 | Ziaylek et al. | ............ | 248/316.1 |
| 6,883,766 B1 * | 4/2005 | Ziaylek et al. | ............ | 248/313 |
| 6,926,243 B1 * | 8/2005 | Ziaylek et al. | ............ | 248/307 |
| D536,502 S * | 2/2007 | Weigand et al. | ............ | D34/27 |
| 7,922,246 B2 * | 4/2011 | Gale et al. | ............ | 297/188.06 |
| 2009/0020575 A1 | 1/2009 | Katchen et al. | | |

* cited by examiner

*Primary Examiner* — Anita M King
(74) *Attorney, Agent, or Firm* — Crossley Patent Law; Mark A. Crossley

(57) ABSTRACT

The oxygen tank accessory apparatus provides a basket with accompanying hand-operated clamps for affixing the apparatus to an existing supported oxygen tank, such as those attached to vehicles like wheelchairs. The components of the apparatus are made of appropriate materials that meet medical standards and medical environment standards. Both the clamps and the basket are designed to be lightweight. The clamp's opposing convex clamp members, for example, have central cutouts to further save weight. The clamp members are interiorly lined with a frictional material for best tank retention until removal is desirable. The levers with curved extensions provide for a user to easily lever the clamp members away from an oxygen tank so that the apparatus can be easily applied and removed without tools or inordinate physical effort.

14 Claims, 5 Drawing Sheets

OXYGEN TANK ACCESSORY APPARATUS

BACKGROUND OF THE INVENTION

Various clamps and devices for holding an oxygen tank to a portable vehicle, such as a wheelchair, are widely used. A problem exists for vehicle users though, in that many such individuals also use oxygen, carry catheters and associated equipment, and other medical necessities. The present apparatus provides an oxygen tank accessory that removably clamps to a supported oxygen tank while providing for carriage of oxygen hose, and medical and other equipment.

FIELD OF THE INVENTION

The oxygen tank accessory apparatus relates to oxygen tanks and more especially to an oxygen tank apparatus that removably clamps to an oxygen tank and provides for storing and carrying various necessities and conveniences, especially oxygen hoses and other medically oriented items.

SUMMARY OF THE INVENTION

The general purpose of the oxygen tank accessory apparatus, described subsequently in greater detail, is to provide an oxygen tank accessory apparatus which has many novel features that result in an improved oxygen tank accessory apparatus which is not anticipated, rendered obvious, suggested, or even implied by prior art, either alone or in combination thereof.

To attain this, the oxygen tank accessory apparatus provides a basket with accompanying hand-operated clamps for affixing the apparatus to an existing supported oxygen tank and also to a tank with a cover, especially those tanks attached to a vehicle such as a wheelchair. The components of the apparatus may be made of plastic, metal, composites, and other appropriate materials that meet medical standards and medical environment standards. Both the clamps and the basket are designed to be lightweight. The clamp's opposing convex clamp members, for example, have central cutouts to further save weight. The clamp members are interiorly lined with a frictional material for best tank retention until removal is desirable. The levers with curved extensions provide for a user to easily lever the clamp members away from an oxygen tank so that the apparatus can be easily applied and removed. The clamp members are convex for best grip.

Thus has been broadly outlined the more important features of the improved oxygen tank accessory apparatus so that the detailed description thereof that follows may be better understood and in order that the present contribution to the art may be better appreciated.

An object of the oxygen tank accessory apparatus is to removably clamp to a supported oxygen tank.

Another object of the oxygen tank accessory apparatus is to provide for carriage of medical equipment and other accessories.

A further object of the oxygen tank accessory apparatus is to meet medical standards for use.

An added object of the oxygen tank accessory apparatus is to negate sharp edges.

And, an object of the oxygen tank accessory apparatus is to automatically hold onto an oxygen tank until manually removed via expandable clamps.

A further object of the oxygen tank accessory apparatus is to be manually added to and removed from tanks, without tools.

An object of the oxygen tank accessory apparatus is to assist in holding onto a tank or tank cover via a frictional material.

These together with additional objects, features and advantages of the improved oxygen tank accessory apparatus will be readily apparent to those of ordinary skill in the art upon reading the following detailed description of presently preferred, but nonetheless illustrative, embodiments of the improved oxygen tank accessory apparatus when taken in conjunction with the accompanying drawings.

In this respect, before explaining the current embodiments of the improved oxygen tank accessory apparatus in detail, it is to be understood that the oxygen tank accessory apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved oxygen tank accessory apparatus. It is therefore important that the claims be regarded as including such equivalent constructions insofar as they do not depart from the spirit and scope of the oxygen tank accessory apparatus. It is also to be understood that the phraseology and terminology employed herein are for purposes of description and should not be regarded as limiting.

DETAILED DESCRIPTION OF THE DRAWINGS

With reference now to the drawings, and in particular FIGS. 1 through 5 thereof, the principles and concepts of the oxygen tank accessory apparatus generally designated by the reference number 10 will be described.

Figure 1:
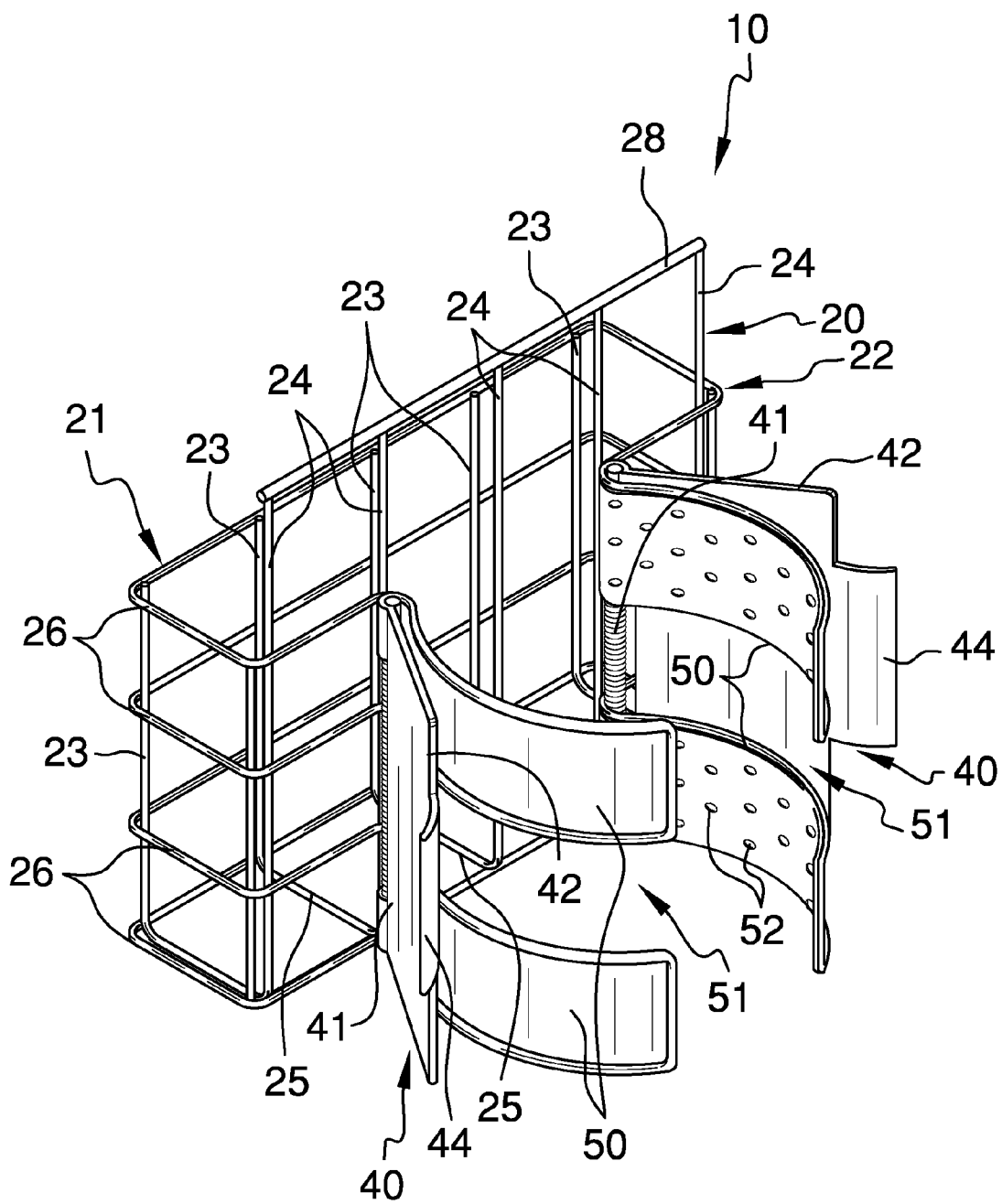
FIG. 1 is a perspective view.

Referring to FIG. 1, the apparatus 10 partially comprises the rectangular basket 20 having a front 21 spaced apart from the back 22. The basket 20 further comprises the plurality of vertically spaced apart rectangular horizontal members 26. The plurality of spaced apart front vertical members 23 is disposed between and connected to the horizontal members 26 at the basket 20 front 21. Each front vertical member 23 is further extended horizontally to the basket 20 back 22 via a horizontal extension 25.

Figure 2:
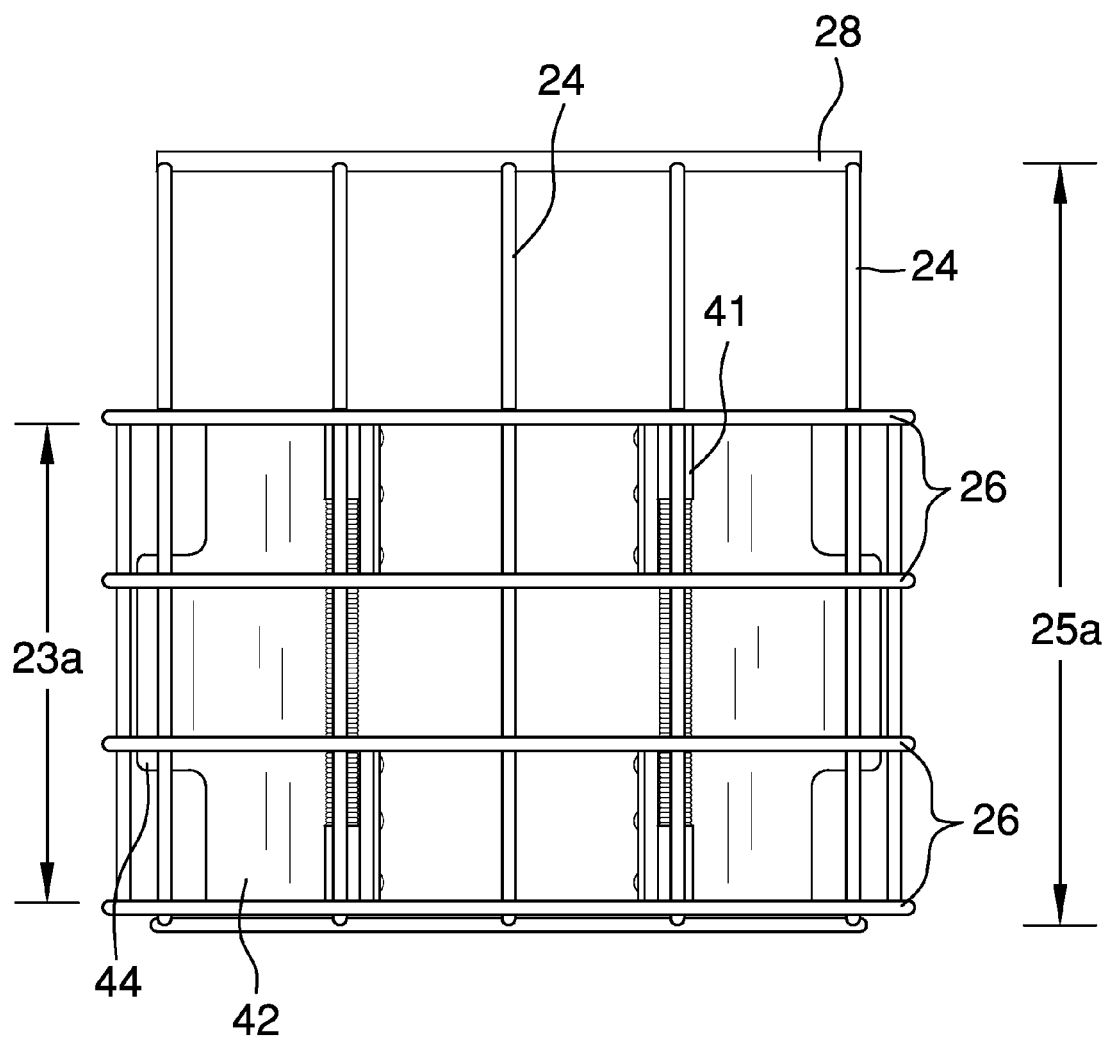
FIG. 2 is a frontal elevation view.
Figure 3:
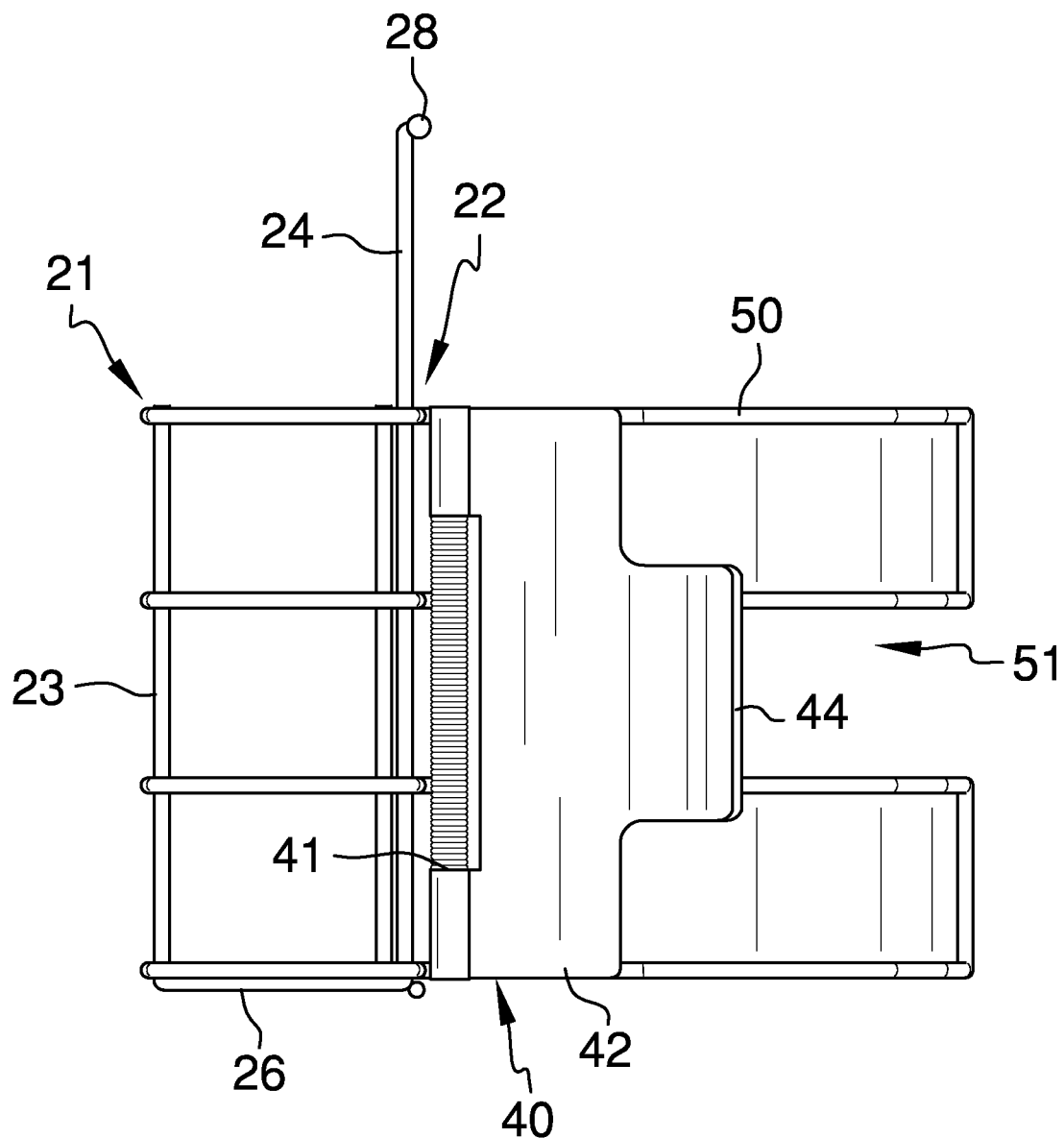
FIG. 3 is a lateral elevation view.
Figure 4:
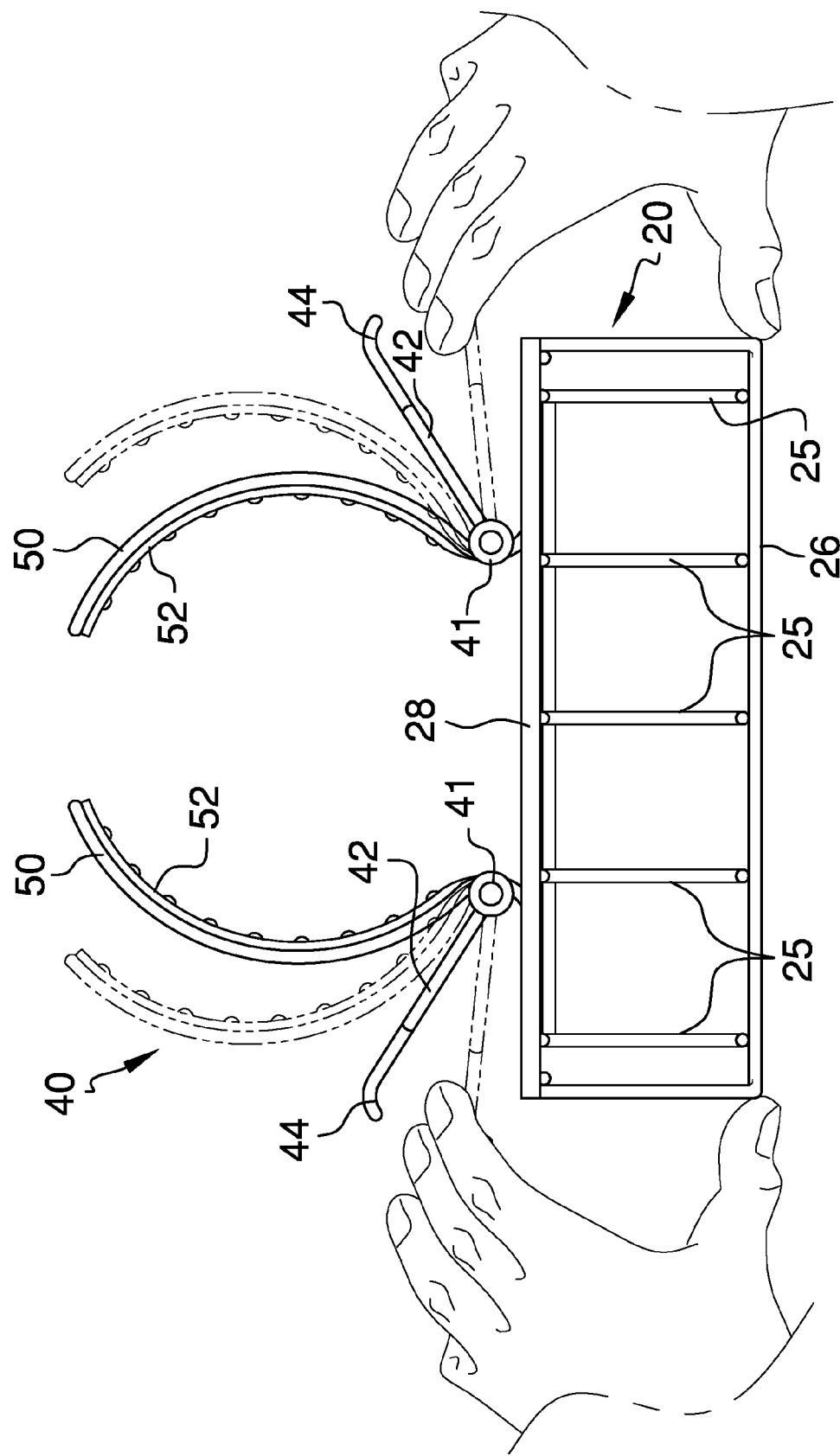
FIG. 4 is a top plan view.
Figure 5:
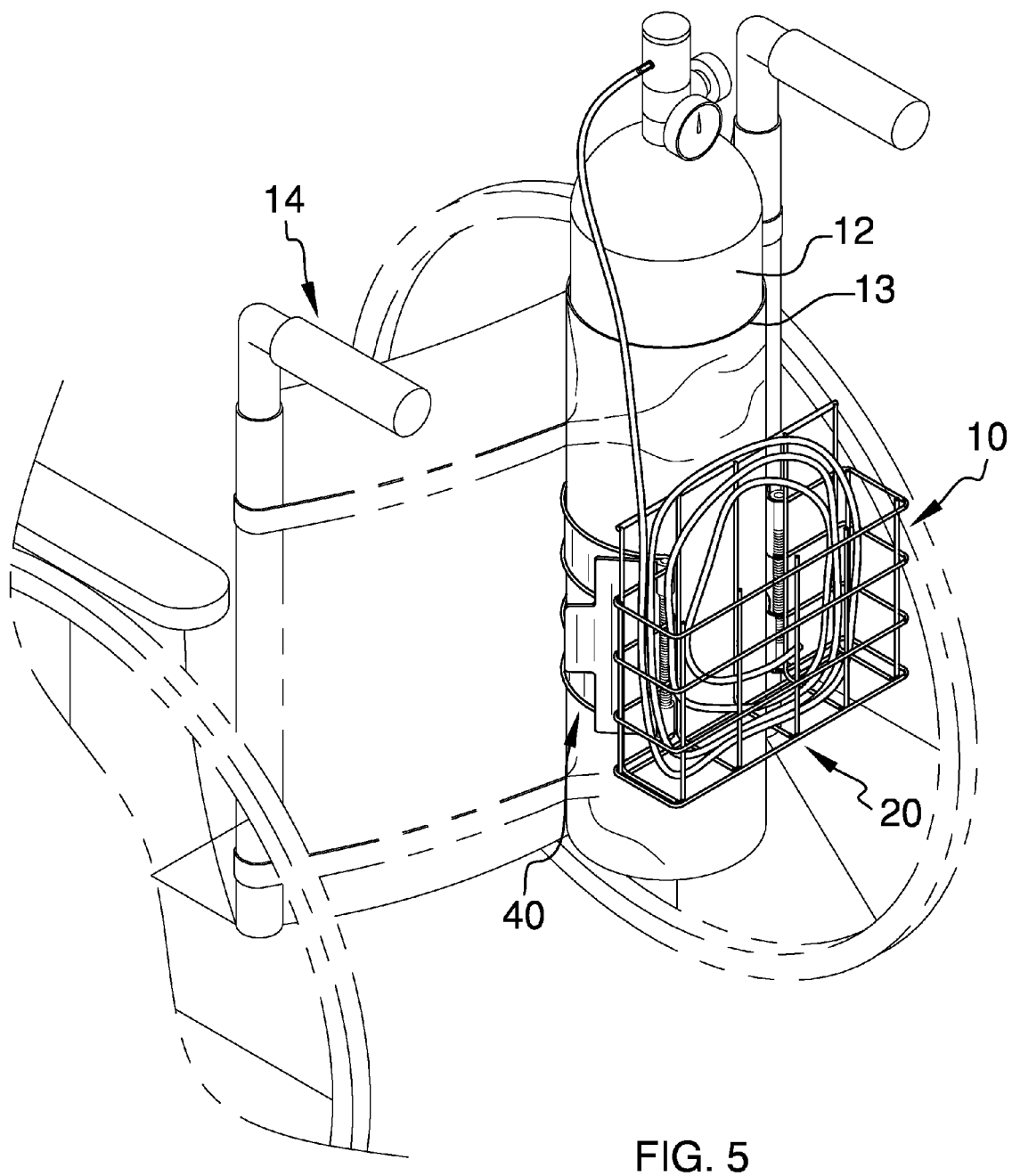
FIG. 5 is a perspective view of the apparatus affixed to a tank cover and tank that is mounted to a wheelchair.

Referring to FIG. 2, the front vertical members 23 have a front vertical member length 23a.

Referring again to FIGS. 1 and 2, the plurality of spaced apart back vertical members 24 are disposed between and connected to the horizontal members 26 at the basket 20 back 22. The back vertical members 24 have a back vertical member length 25a. The back vertical member length 25 is less than the front vertical member length 23. The upper horizontal fence 28 is disposed above and connected to the back vertical members 24.

Referring to FIGS. 4 and 5, and again to FIG. 1, the pair of opposed clamps 40 is affixed to the basket 20 back 22 via the spring-loaded hinges 41. One hinge 41 connects each clamp 40 to the basket 20.

Each clamp 40 has a convex clamp member 50 shaped opposite that of the opposed clamp member 50 such that the convex faces medially. For weight reduction, each clamp member 50 further comprises a horizontally disposed center cutout 51.

The clamp members 50 are held to an existing oxygen tank 12 by the spring-loaded hinges 41. A lever 42 is affixed laterally to each clamp member 50. The interior frictional material 52 is disposed on each clamp member 50. An outward curved extension 44 is disposed on each lever 42. The spring-loaded hinges 41 are overcome in manually expanding the clamp members 50 apart by leveraging the curved extensions toward the basket 20 front 21 to release the apparatus 10 from the oxygen tank 12. The apparatus 10 is not hindered in clamping the tank 12 by the existing tank cover 13 that can either be a part of the existing wheel chair 14 or simply a tank cover 13.

With respect to the above description then, it is to be realized that the optimum dimensional relationships for the parts of the oxygen tank accessory apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the oxygen tank accessory apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the oxygen tank accessory apparatus may be used.

Therefore, the foregoing is considered as illustrative only of the principles of the oxygen tank accessory apparatus. Further, since numerous modifications and changes will readily occur to those skilled in the art, it is not desired to limit the oxygen tank accessory apparatus to the exact construction and operation shown and described, and accordingly, all suitable modifications and equivalents may be resorted to, falling within the scope of the oxygen tank accessory apparatus.

What is claimed is:

1. An oxygen tank accessory apparatus, comprising, in combination:
   a basket comprised of spaced apart members, the basket having a front spaced apart from a back;
   a pair of opposed clamps affixed to the basket back via spring-loaded hinges, each clamp having a convex clamp member shaped opposite that of the opposed clamp member, the clamp members held to an existing oxygen tank by the spring-loaded hinges;
   means for spreading the convex clamp members in overcoming the spring-loaded hinges to release the clamp members from the oxygen tank.

2. The apparatus according to claim 1 further comprising a horizontal cutout within each convex clamp member.

3. The apparatus according to claim 1 wherein the convex clamp members further comprise an interiorly disposed frictional material.

4. The apparatus according to claim 2 wherein the convex clamp members further comprise an interiorly disposed frictional material.

5. The apparatus according to claim 1 wherein the means for spreading the convex clamp members further comprises a manual mechanism operated by hands only.

6. The apparatus according to claim 2 wherein the means for spreading the convex clamp members further comprises a manual means operated by hands only.

7. The apparatus according to claim 3 wherein the means for spreading the convex clamp members further comprises a manual means operated by hands only.

8. The apparatus according to claim 4 wherein the means for spreading the convex clamp members further comprises a manual means operated by hands only.

9. An oxygen tank accessory apparatus, comprising, in combination:
   a rectangular basket having a front spaced apart from a back, the basket further comprising:
      a plurality of vertically spaced apart rectangular horizontal members;
      a plurality of spaced apart front vertical members disposed between and connected to the horizontal members at the basket front, each front vertical member further extended horizontally to the basket back via a horizontal extension;
      a plurality of spaced apart back vertical members disposed between and connected to the horizontal members at the basket back;
   a pair of opposed clamps affixed to the basket back via spring-loaded hinges, each clamp having a convex clamp member shaped opposite that of the opposed clamp member, the clamp members held to an existing oxygen tank by the spring-loaded hinges;
   means for spreading the convex clamp members in overcoming the spring-loaded hinges to release the clamp members from the oxygen tank.

10. The apparatus according to claim 9 wherein the back vertical members further comprise a back vertical member length greater than a front vertical member length of the front vertical members.

11. An oxygen tank accessory apparatus, comprising, in combination:
   a rectangular basket having a front spaced apart from a back, the basket further comprising:
      a plurality of vertically spaced apart rectangular horizontal members;
      a plurality of spaced apart front vertical members disposed between and connected to the horizontal members at the basket front, each front vertical member further extended horizontally to the basket back via a horizontal extension, the front vertical members having a front vertical member length;
      a plurality of spaced apart back vertical members disposed between and connected to the horizontal members at the basket back, the back vertical members having a back vertical member length;
   a pair of opposed clamps affixed to the basket back via spring-loaded hinges, each clamp having a convex clamp member shaped opposite that of the opposed clamp member, the clamp members held to an existing oxygen tank by the spring-loaded hinges;
   a lever affixed laterally to each clamp member;
   an interior frictional material disposed on each clamp member;
   an outward curved extension on each lever;
   whereby the spring-loaded hinges are overcome in manually expanding the clamp members apart to release the apparatus from the oxygen tank.

12. The apparatus according to claim 11 wherein each clamp member further comprises a horizontally disposed center cutout.

13. The apparatus according to claim 11 wherein the back vertical member length is further greater than the front vertical member length;

an upper horizontal fence disposed above and connected to the back vertical members.

14. The apparatus according to claim 12 wherein the back vertical member length is further greater than the front vertical member length;
an upper horizontal fence disposed above and connected to the back vertical members.

* * * * *